United States Patent
Kuo et al.

(10) Patent No.: US 7,432,088 B2
(45) Date of Patent: Oct. 7, 2008

(54) METHODS FOR THE PRODUCTION OF ANSAMITOCINS

(75) Inventors: Cynthia Kuo, Lujou (TW); Graham S. Byng, Snohomish, WA (US); Wayne C. Widdison, Somerville, MA (US)

(73) Assignee: Immunogen Inc., Waltham, MA (US)

( * ) Notice: Subject to any disclaimer, the term of this patent is extended or adjusted under 35 U.S.C. 154(b) by 218 days.

(21) Appl. No.: 11/037,104

(22) Filed: Jan. 19, 2005

(65) Prior Publication Data

US 2005/0170475 A1    Aug. 4, 2005

Related U.S. Application Data

(63) Continuation-in-part of application No. 10/840,768, filed on May 7, 2004, now abandoned.

(60) Provisional application No. 60/468,638, filed on May 8, 2003.

(51) Int. Cl.
*C12P 17/18* (2006.01)
*C12P 17/16* (2006.01)
*C12N 1/20* (2006.01)

(52) U.S. Cl. .................... 435/119; 435/118; 435/252.1; 435/253.2; 540/460; 540/462

(58) Field of Classification Search ................. 435/118, 435/119, 252.1, 253.2; 540/460, 462
See application file for complete search history.

(56) References Cited

U.S. PATENT DOCUMENTS

| | | | |
|---|---|---|---|
| 4,151,042 | A | 4/1979 | Higashide et al. |
| 4,294,757 | A | 10/1981 | Asai |
| 4,307,016 | A | 12/1981 | Asai et al. |
| 4,322,348 | A | 3/1982 | Asai et al. |
| 4,331,598 | A | 5/1982 | Hasegawa et al. |
| 4,361,650 | A | 11/1982 | Asai et al. |
| 4,424,219 | A | 1/1984 | Hashimoto et al. |
| 5,208,020 | A | 5/1993 | Chari et al. |
| 5,416,064 | A | 5/1995 | Chari et al. |
| 6,333,410 | B1 | 12/2001 | Chari et al. |
| 6,441,163 | B1 | 8/2002 | Chari et al. |
| 6,573,074 | B2 | 6/2003 | Fulston et al. |
| 7,192,750 | B2 * | 3/2007 | Chung et al. ............... 435/119 |
| 2002/0015984 | A1 * | 2/2002 | Fulston et al. .............. 435/120 |
| 2002/0156274 | A1 | 10/2002 | Terfloth |
| 2003/0157669 | A1 | 8/2003 | Fulston |
| 2004/0235840 | A1 | 11/2004 | Chari et al. |

FOREIGN PATENT DOCUMENTS

| | | |
|---|---|---|
| CA | 2006408 | 6/1990 |
| DE | 2241418 A1 | 3/1974 |
| DE | 27 46 253 A1 | 10/1978 |
| EP | 26338 A1 | 4/1981 |
| JP | 53124692 A2 | 10/1978 |
| JP | 55029972 A2 | 3/1980 |
| WO | 2001095943 A2 | 12/2000 |
| WO | 2001068142 A1 | 9/2001 |

OTHER PUBLICATIONS

Yu et al "The biosynthetic gene cluster of the maytansinoid antitumor agent ansamitocin form Actinosynnema pretiosum" PNAS, Jun. 11, 2002, vol. 99, No. 12.*
Abbott B. Huang, et al., "Maytansine Inhibits Nucleotide Binding at the Exchangeable Sit of Tubulin," *Biochem. Biophys. Res.*, (Commun. (1985), 128:(3), pp. 1239-46.
Akiyoshi Kawai, "Chemical Modification of Ansamitocins. I. Synthesis and Properties of 4,5-deoxymaytansinoids," *Chem. Pharm. Bull*, 1984, 32:(6), pp. 2194-2199.
Akiyoshi Kawai, et al., "Chemical Modification of Ansamitocins. III. Synthesis and Biological Effects of 3-Acyl Esters of Maytansinol," *Chem. Pharm. Bull*, 1984, 32:(9), pp. 3441-3451.
Guenter Adam, "Biologically Active Natural Products as Synthetic Models in Active Substance Development," *Z. Chem.*, 1981, 21:(8), pp. 273-281.
Masayuki Shimagaki, "2-Halovinyl Aryl Sulfones: New Coupling Reagents for Caboxamide Formation," *Phosphorus Sulfur*, 1983, 16:(1-2), pp. 45-48.
MetaChem Technologies, Inc., Liquid Chromatography, HPLC, IC, CE Column Guide, pp. 53-54 (2000/2001).
S. Morris Kupchan, et al., "Structural Requirements for Antileukemic Activity among the Naturally Occurring and Semisynthetic Maytansinoids," *Journal of Medicinal Chemistry*, 1978, 21:(1), pp. 31-37.
Troels Skrydstrup, "The Opening of Trans-2-3-eopoxy-1-butanol Derivatives with Organometallic Reagents," *Tetrahedron Lett.*, 1990, 31:(49), pp. 7145-7148.
Xuegin Gu, "Studies on the Total Syntheses of Maytansinoids. (III). Synthesis of C5-N Fragment," *Sci. Sin.*, Ser. B (Engl. Ed.), 1998, 31:(11), pp. 1333-1341.
International Search Report dated Jun. 21, 2006.

* cited by examiner

*Primary Examiner*—Herbert J. Lilling
(74) *Attorney, Agent, or Firm*—Sughrue Mion, PLLC

(57) ABSTRACT

A process of the large-scale fermentation of a highly productive ansamitocin-producing strains. A method for isolating crude ansamitocins. A method for purifying ansamitocins.

35 Claims, 1 Drawing Sheet

Fig. 1 Structures of Ansamitocins
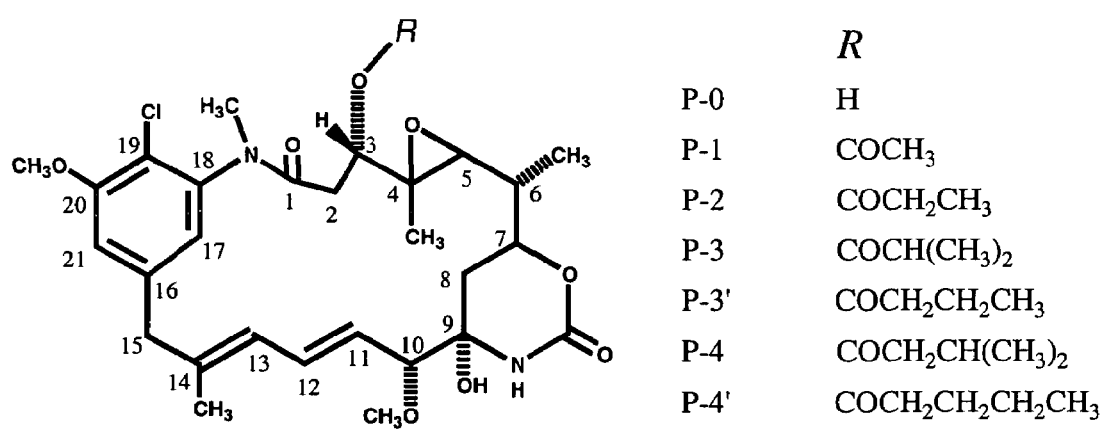
| | R |
|---|---|
| P-0 | H |
| P-1 | COCH$_3$ |
| P-2 | COCH$_2$CH$_3$ |
| P-3 | COCH(CH$_3$)$_2$ |
| P-3' | COCH$_2$CH$_2$CH$_3$ |
| P-4 | COCH$_2$CH(CH$_3$)$_2$ |
| P-4' | COCH$_2$CH$_2$CH$_2$CH$_3$ |

US 7,432,088 B2

METHODS FOR THE PRODUCTION OF ANSAMITOCINS

This is a Continuation-in-part application of U.S. application Ser. No. 10/840,768, filed May 7, 2004, now abandoned, which claims priority to U.S. Provisional Application No. 60/468,638 filed May 8, 2003, the disclosure of both of which is incorporated herein in its entirety by reference.

FIELD OF THE INVENTION

The invention relates to processes for the production of Ansamitocins. Ansamitocins refer to a mixture of ansamitocins that differ in their C-3 ester side-chain. Ansamitocins can be converted into the C-3 alcohol maytansinol.

BACKGROUND OF THE INVENTION

Ansamitocins are highly cytotoxic compounds derived from fermentation of microorganisms such as *Actinosynnema pretiosum*. Ansamitocins have been chemically converted into thiol-containing maytansinoids, whose therapeutic use in the form of cell binding agent-maytansinoid conjugates has been described (U.S. Pat. Nos. 5,208,020; 5,416,064; 6,333,410; and 6,441,163).

The fermentation process with *Actinosynnema* spp strains such as *Actinosynnema pretiosum* produces several ansamitocin species bearing different ester substituents at C-3 (FIG. 1). The various C-3 esters produced include P-3 (iso-butyryl), P-3' (n-butyryl), P-2 (propionyl), P-4 (iso-valeryl), P-4' (n-valeryl). All of these esters can be reductively cleaved to give the C-3 alcohol maytansinol (P-0), which is the precursor for the synthesis of thiol-containing maytansinoids. In addition, minor amounts of undesired ansamitocins which are modified at other sites, such as N-demethyl, 20-O-demethyl, and 19-dechloro are produced. Upon reductive de-acylation, these ansamitocins do not produce maytansinol.

Processes for the production of ansamitocin from fermentation of *Actinosynnema* spp have been described (U.S. Pat. Nos. 4,162,940; 4,450,234; 4,228,239; 4,331,598; and 4,356,265). The yield of ansamitocins produced varies, with titers generally ranging from 12 mg/L to 100 mg/L. The ansamitocins are typically recovered and purified by a multistep process involving addition of a filter aid and an organic solvent to the whole fermentation broth, followed by concentrating the organic layer and precipitation with petroleum ether. The precipitate was further purified using silica chromatography and crystallization, followed by further purification by recrystallization or chromatography.

Thus, the process is cumbersome and involves several steps where highly toxic material has to be handled. This renders the scale up of such a process very difficult. In addition, the safety of the human operator has to be ensured throughout the various processing steps.

A recent application (US 2002/0015984 A1) claims certain improvements in the process for the production of ansamitocins. The ansamitocin titers in the fermentation broth are reported to have ranged from 65 to 86 mg/L. The claimed improvements included heat inactivation of the broth at 75° C., extraction into an aromatic hydrocarbon solvent such as toluene, chromatography through an open silica column, followed by crystallization. In order to reduce the cost of ansamitocin production, new *Actinosynnema* spp strains that give significantly higher titers (up to 400 mg/L in fermenters) than those previously described, have been produced. The processes previously described for the production of ansamitocins have several drawbacks, and thus cannot be adapted for the new high producing strains that have been developed. For example, heat inactivation at 75° C. results in some degradation of ansamitocin and a 10 to 20% loss in yield. Extraction of fermentation broth containing high ansamitocin content with aromatic hydrocarbons is inefficient and incomplete, since the ansamitocins are not highly soluble in such solvents. Purification of ansamitocins on open self-packed silica columns has two drawbacks: 1) lot to lot variability in purity and recovery, and 2) significant human exposure resulting in safety concerns. Thus, a need exists to produce ansamitocins in high yields and also to provide an efficient process for its isolation and purification, while minimizing worker exposure to the highly toxic drug.

SUMMARY OF THE INVENTION

One aspect of the invention is a process for the large-scale fermentation of ansamitocin-producing microorganisms, the process being especially applicable to a new, highly productive ansamitocin-producing strain.

Another aspect of the invention is a method for isolating the crude ansamitocin, and for preparing purified ansamitocins comprising the following steps:

1) optional inactivation of the culture, for example, by exposure to heat at about 50° to 55° C. or by addition of 1% by volume of chloroform, 2) extraction with a non-aromatic organic solvent, 3) concentration of the extract, 4) purification of the concentrate on a silica or alumina column, preferably a pre-packed silica cartridge column, and 5) crystallization of the product.

Other aspects of the invention include the following:

A process for preparing purified ansamitocins comprising the steps of:

1) Culturing an ansamitocin-producing microorganism in a liquid culture medium;
2) Extracting ansamitocins from the culture medium with a non-aromatic water immiscible solvent;
3) Concentrating the extracted ansamitocins; and
4) Purifying the ansamitocins by any one of a), b), c) and d):
   a) adsorption chromatography over silica gel or alumina,
   b) crystallization,
   c) adsorption chromatography over silica gel or alumina followed by crystallization, and
   d) crystallization followed by adsorption chromatography over silica gel or alumina.

A process for preparing purified ansamitocins comprising the steps of:

1) Culturing an ansamitocin-producing microorganism in a liquid culture medium;
2) Extracting ansamitocins from the culture medium with a non-aromatic water immiscible solvent;
3) Concentrating the extracted ansamitocins; and
4) Purifying the ansamitocins by any one of a), b), c) and d):
   a) adsorption chromatography over silica gel or alumina,
   b) crystallization,
   c) adsorption chromatography over silica gel or alumina followed by crystallization, and
   d) crystallization followed by adsorption chromatography over silica gel or alumina.

A process for preparing purified ansamitocins comprising the steps of:

1) Culturing an ansamitocin-producing microorganism in a liquid culture medium;
2) Extracting ansamitocins from the culture medium with a non-aromatic water immiscible solvent;
3) Concentrating the extracted ansamitocins; and 4) Purifying the ansamitocins by adsorption chromatography over silica gel or alumina followed by crystallization.

A process for preparing purified ansamitocins comprising the steps of:
1) Culturing an ansamitocin-producing microorganism in a liquid culture medium;
2) Extraction of ansamitocins from the culture medium with a non-aromatic water immiscible solvent;
3) Filtration to remove solids, allowing isolation of the organic phase
4) Concentration of ansamitocins from the organic phase; and
5) Purifying the ansamitocins by any one of a), b), c) and d):
   a) adsorption chromatography over silica gel or alumina,
   b) crystallization,
   c) adsorption chromatography over silica gel or alumina followed by crystallization, and
   d) crystallization followed by adsorption chromatography over silica gel or alumina.

A process for preparing purified ansamitocins comprising the steps of:
1) Culturing an ansamitocin-producing microorganism in a liquid culture medium;
2) Extracting ansamitocins from the culture medium with a non-aromatic water immiscible solvent, using various centrifugation techniques;
3) Concentrating the extracted ansamitocins; and
4) Purifying the ansamitocins by any one of a), b), c) and d):
   a) adsorption chromatography over silica gel or alumina,
   b) crystallization,
   c) adsorption chromatography over silica gel or alumina followed by crystallization, and
   d) crystallization followed by adsorption chromatography over silica gel or alumina.

A process for preparing purified ansamitocins comprising the steps of:
1) Culturing an ansamitocin-producing microorganism in a liquid culture medium;
2) Centrifuging the broth in the presence of one or more water miscible organic solvents to remove solids while retaining ansamitocins in solution.
3) Adding a water immiscible non-aromatic solvent, to allow extraction of ansamitocins into the organic layer. Optionally, various salts or other components could also be added to the organic phase during the extraction.
4) Concentrating the extracted ansamitocins; and
5) Purifying the ansamitocins by any one of a), b), c) and d):
   a) adsorption chromatography over silica gel or alumina,
   b) crystallization,
   c) adsorption chromatography over silica gel or alumina followed by crystallization, and
   d) crystallization followed by adsorption chromatography over silica gel or alumina.

A process for preparing purified ansamitocins comprising the steps of:

1) Culturing an ansamitocin-producing microorganism in a liquid culture medium;
2) Optional treatment of the culture medium to facilitate extraction of ansamitocins;
3) Solid phase extraction of ansamitocins from the culture medium onto a resin;
4) Isocratic or gradient elution of ansamitocins from the resin using one or more organic solvents or one or more organic solvents combined with water;
5) Concentrating the extracted ansamitocins; and
6) Optionally purifying the ansamitocins further by any one of a), b), c) and d):
   a) adsorption chromatography over silica gel or alumina,
   b) crystallization,
   c) adsorption chromatography over silica gel or alumina followed by crystallization, and
   d) crystallization followed by adsorption chromatography over silica gel or alumina.

In these embodiments the invention may optionally include:

(i) chemical or heat inactivation of the microorganisms in the fermentation broth;
(ii) treatment of the culture medium to facilitate solvent extraction of ansamitocins, prior to step 2; or
(iii) a washing step in which a crude solution of ansamitocins in organic solvent is washed with water, an aqueous salt solution, an aqueous acid or an aqueous base in any sequential combination, either before or after the precipitation. This step can be performed at various stages of the purification.

A process for extracting ansamitocins from fermentation broth, said process comprising:

1) Optionally inactivating ansamitocin-producing microorganisms in the fermentation broth; and
2) Extracting the ansamitocins from the fermentation broth with a non-aromatic water-immiscible solvent.

The above process may also include treatment of the culture medium to facilitate solvent extraction of ansamitocins, prior to step 2.

A process for extracting ansamitocins from fermentation broth, said process comprising:

1) Extraction of ansamitocins from the fermentation broth with a non-aromatic water-immiscible solvent.Filtration to remove solids, allowing isolation of the organic phase.
2) Filtration to remove solids, allowing isolation of the organic phase.

The above process may optionally include:

(i) chemical or heat inactivation of the microorganisms in the fermentation broth; and/or
(ii) treatment of the culture medium to facilitate solvent extraction of ansamitocins, prior to step 2.

A process for extracting ansamitocins from fermentation broth, said process comprising: extracting ansamitocins from the culture medium by various centrifugation techniques with a non-aromatic water immiscible solvent.

The above process may optionally include:

(i) chemical or heat inactivation of the microorganisms in the fermentation broth; and/or
(ii) treatment of the culture medium to facilitate solvent extraction of ansamitocins, prior to or during centrifugation.

A process for removing solid debris from fermentation broth, said process comprising:

1) Centrifugation of the fermentation broth in the presence of a water miscible organic solvent to remove solids while retaining ansamitocins in solution.

The above process may optionally include:

(i) chemical or heat inactivation of the microorganisms in the fermentation broth; and/or
(ii) treatment of the culture medium to facilitate solvent extraction of ansamitocins, prior to or during centrifugation.

In the above-described methods, it is preferred that the ansamitocin-producing microorganism is *Actinosynnema* spp., more preferably *Actinosynnema pretiosum*. The ansamitocin-producing microorganism may also be *Actinosynnema*

*pretiosum* ATCC 31565 or strains derived therefrom or *Actinosynnema pretiosum* PF4-4 (ATCC PTA-3921) or strains derived therefrom. As described in U.S. Pat. No. 4,450,234, *Actinosynnema pretiosum* ATCC 31565 was deposited with (i) Institute for Fermentation, Osaka, 17-85, Juso-honmachi 2-chome, Yodogawa-ku, Osaka 532-8686, Japan, on Aug. 20, 1979, under the accession number of IFO 13963; (ii) National Institute of Bioscience and Human Technology (formerly Fermentation Research Institute), Agency of Industrial Science and Technology, Ministry of International Trade and Industry, 1-3, higashi 1-chome, Tsukuba-shi, Ibaraki-ken 305, Japan, on Aug. 29, 1979, under the accession number of FERM-P NO. 5185; and (iii) the American Type Culture Collection, 10801 University Blvd., Manassas, Va. 20110-2209, USA, on Sep. 11, 1979, under the accession number of ATCC 31565. In addition, *Actinosynnema pretiosum* PF4-4 was deposited under the provisions of the Budapest Treaty with the American Type Culture Collection, 10801 University Blvd., Manassas, Va. 20110-2209, USA, on Dec. 11, 2001, and has been accorded Accession No. ATCC PTA-3921.

BRIEF DESCRIPTION OF THE DRAWINGS

FIG. 1 shows the structure of various ansamitocin C-3 esters that can be made by fermentation, as well as the C-3 alcohol, maytansinol (P-0).

DETAILED DESCRIPTION OF THE INVENTION

Methods are provided for culturing a microorganism highly productive for ansamitocins in a liquid culture medium in large fermenters. Methods are also provided for the extraction of the ansamitocin from the culture broth and the microorganism into a non-aromatic water-immiscible organic solvent in which the ansamitocin is highly soluble, and for the purification of the ansamitocin by passage through a silica or an alumina column if needed, preferably these columns are pre-packed cartridges, followed by crystallization of the product. If necessary, the microorganism may be inactivated by heat treatment or treatment with chloroform prior to the extraction step.

The purified ansamitocins which could include a mixture of various C-3 esters, such as ansamitocins P-3, P-3', P-4, P-4', P-2 and P-1 (FIG. 1), may be treated with a reducing agent to give the desired C-3 hydroxyl compound, maytansinol (P-0). The purified ansamitocins typically contain only minor amounts of undesirable ansamitocins that have modifications on sites of the molecule other than the C-3 position. Preferably, the ansamitocin-producing strain is *Actinosynemma* spp. More preferably, the microorganism is *Actinosynnema pretiosum*. The microorganism can also be *Actinosynnema pretiosum* PF4-4 (ATCC PTA-3921) and derivatives thereof and *Actinosynnema pretiosum* ATCC 31565 and derivatives thereof. The microorganism can be grown by fermentation culture techniques that are known to those of ordinary skill in the art, using the specific media described herein or any other media that is described in the art (U.S. Pat. Nos. 4,162,940; 4,450,234; 4228,239; 4,331,598; and 4,356,265).

One embodiment of the method of the invention is the culture of the microorganism in a liquid culture medium. Growth of the bacterial strain PF4-4 is performed under controlled conditions and can employ a wide variety of media and conditions. For example, PF4-4 can be grown under similar conditions and with similar media to those described for ATCC 31565 or ATCC 31281 in issued U.S. Pat. Nos. 4,137,230; 4,162,940; 4,331,598; 4,356,265; and 4,450,234; and as described in Hatano et al., Agric. Biol. Chem. 48, 1721-1729, 1984. Thus, the strain PF4-4 tolerates a wide variety of carbon sources, which also support fermentative production of ansamitocins. Exemplary growth media are given in Tables 1 and 2. Table 1 shows media that support production of ansamitocins by ansamitocin-producing microorganisms, such as *Actinosynnema pretiosum* PF4-4 and Table 2 shows further media suitable for the propagation and/or growth of *Actinosynnema pretiosum* PF4-4, and other ansamitocin-producing microorganisms.

TABLE 1

Production Media Composition (entries are % w/v).

| | FM 27-44 | FM 112-37 | FM 4-4 | FM 4-6 | FM 4-7 |
|---|---|---|---|---|---|
| Dextrin (Lodex-5) | 6 | 6 | 5 | 5 | 5 |
| Maltose (Difco) | 4 | 4 | 2 | 2 | 2 |
| Proflo (Traders) | | | 2.0 | 2.5 | 2.75 |
| Soybean Flour (ADM) | 1.5 | 2.0 | | | |
| Pharmamedia (Traders) | 0.5 | | | | |
| CSP (Roquette) | 0.5 | 0.5 | 0.5 | 0.15 | 0.15 |
| P. Dry Yeast (Difco) | 0.25 | | | | |
| $MgSO_4 \cdot 7H_2O$ (Wako) | 0.05 | | | | |
| $CaCO_3$ (Hayashi) | | | 0.5 | 0.5 | 0.6 |
| $(NH_4)_2SO_4$ (Wako) | | 0.05 | | | |
| $KH_2PO_4$ (Wako) | 0.05 | 0.04 | | | |
| $K_2HPO_4$ (Wako) | | 0.05 | 0.06 | 0.06 | 0.06 |
| $CaCl_2 \cdot 2H_2O$ (Wako) | 0.5 | 0.5 | | | |
| $NaHCO_3$ (Wako) | | 0.2 | | | |
| Zeolite | 0.1 | | | | |
| $FeSO_4 \cdot 7H_2O$ (Wako) | 0.0002 | 0.0002 | 0.0002 | 0.0002 | 0.0002 |
| $ZnSO_4 \cdot 7H_2O$ | 0.0002 | | | | |
| $CoCl_2 \cdot 6H_2O$ (Baker) | 0.001 | | | 0.0005 | 0.0005 |
| Nicotinic Acid | 0.0002 | | | | |
| $MnSO_4 \cdot H_2O$ | 0.0002 | | | | |
| Isobutanol[1] (Tedoa) | 0.1 | 0.5 | 0.5 | 0.3 | 0.3 |
| SAG471 (Witco) | | 0 | 0.06 | 0.04 | 0.04 |
| pH | 6.8 | 6.8 | 6.8 | 7.2 | 7.35 |

Sterilization was at 121° C. for 20 minutes.
[1]Added last.

TABLE 2

Related Media

| | (%, w/v) |
|---|---|
| Slant and plate culture, CM4-1 Agar | |
| Yeast extract (Difco) | 0.3 |
| Malt extract (Difco) | 0.3 |
| Soytone (Difco) | 0.5 |
| Glycerol (Difco) | 1.0 |
| Bacto Agar (Difco) | 2.0 |
| Adjust pH to 6.5 before sterilization; Sterilization: 121° C., 20 minutes | |

TABLE 2-continued

Related Media

| | (%, w/v) |
|---|---|
| Seed Medium, VM4-1' | |
| Soluble starch (BDH) | 2.0 |
| Glucose (Shuling) | 1.0 |
| Soybean meal (ADM) | 1.0 |
| Corn Steep Liquor (Solulys) | 0.5 |
| Soytone (Difco) | 0.5 |
| NaCl (Wako) | 0.3 |
| CaCO$_3$ (Hayashi) | 0.5 |
| pH 6.8; Sterilization: 121° C., 20 minutes | |

Preferred methods for fermentative production of ansamitocins from strain PF4-4 are further described in EXAMPLES 1 and 2 below.

Fermentation:

The cultivation may be conducted by culture conditions such as, stationary, shaking, aerobic submerged or any other culture conditions. For good culture growth and high production of ansamitocins in large tank fermenters, aerobic submerged culture is preferred. The ansamitocin production can be further enhanced by feeding of nutrients during the fermentation. For example, when cultivating the organism in FM4-6 medium, additional feeding of glucose for the duration of the fermentation or of glucose for about the first 24 to 72 hours, preferably for about the first 48 h, followed by feeding with glucose and a protein nutrient such as cotton seed flour (for example Proflo or Pharmamedia from Trader's Protein, Memphis, Tenn.) or soybean flour, and an alcohol or an aldehyde to facilitate the formation of the C-3 ester side chain, such as isobutanol, isobutyraldehyde, n-butanol, n-butyraldehyde, n-propanol, n-propionaldehyde, isopropanol, isopropionaldehyde, pentanol, valeraldehyde, isopentanol, isovaleraldehyde until the end of the fermentation can result in doubling of the ansamitocin production. While the culture conditions depend on the media used and the production scale, it is normally preferred to carry out the fermentation in the pH range of about 5 to 9, preferably with a starting pH of about 6.5 to 8.0. More preferably, the pH range is about 7 to 8, even more preferably about 7 to 7.4. The most preferred pH is about 7.2. The temperature can range from about 150 to 35° C., with a preferred range of about 25° to 30° C. More preferably, the temperature is about 28° C. The fermentation is continued until the maximum ansamitocin accumulation has been achieved. The cultivation time may vary and depends on several factors including the culture method, the composition of the medium, and the temperature. Typically, the fermentation time ranges from 96 to 336 h.

Analysis of Ansamitocins:

In U.S. Pat. Nos. 4,331,598 and 4,450,234, the parental strain ATCC 31565 is disclosed as producing two classes of ansamitocins that are distinguished by the presence of a methyl or hydroxymethyl group at C-14 (see FIG. 1). For both classes, several different ansamitocins are produced that differ in their respective acyl side chain bound to the C-3 oxygen atom, and with respect to whether C-14 carries a methyl or hydroxymethyl group (or, in subsequent studies, N-demethyl). The nomenclature used herein for the permuted compounds is defined above with reference to FIG. 1.

Ansamitocin P-3 is the major product of PF4-4 and the parental strain ATCC 31565, under certain growth conditions. If the bacteria are grown in the presence of valine or isobutyric acid (see U.S. Pat. No. 4,228,239), or isobutyl alcohol or isobutyraldehyde (see U.S. Pat. No. 4,356,265), other ansamitocin compounds are present only in minor amounts. When PF4-4 strain is grown in different fermentation media (designated FM in Table 1), which all contain isobutyl alcohol, ansamitocin P-3 is the predominant ansamitocin produced. In one method to assay the amount of ansamitocins, samples of the fermentation broths are diluted with ethanol or acetonitrile, then shaken strongly and finally centrifuged. The supernatant is then assayed for ansamitocin P-3 content.

Ansamitocins are preferably fractionated and analyzed by reverse phase high performance liquid chromatography (HPLC), but any suitable technique, such as, for example, MALDI-TOF or thin-layer chromatography may be used. In one method, fermentation broths are extracted with organic solvents, such as ethyl acetate, methylene chloride or chloroform, and the content of P-3 in the organic solvent is determined by HPLC, using reverse phase C18 or C8 columns.

Extraction of Ansamitocins:

Ansamitocins can be extracted from the fermentation broth by methods generally employed for the recovery of secondary metabolites. Since the ansamitocins are readily soluble in non-aromatic solvents, they can be easily extracted by stirring with non-aromatic water-immiscible solvents such as alkyl acetates wherein the alkyl chain is linear or branched and has 1-5 carbon atoms, dialkylketones and halogenated solvents. Examples of suitable alkyl acetates include n-butyl acetate, ethyl acetate, and methyl acetate. An example of a suitable dialkylketone is methyl isobutyl ketone. An example of a suitable halogenated solvent is dichloromethane. Extraction with n-butyl acetate is preferred. Preferably, the ratio of the fermentation broth to the non-aromatic water-immiscible solvent is 1:1 by volume.

Ansamitocins can also be adsorbed from fermentation broth onto various resins, such as, Amberlite XAD-4, XAD-16 commercially available from Rohm and Haas Company, Diaion HP20, HP21, Sepabeads SP825, SP850, SP70, SP700 commercially available from Mitsubishi Chemical Industries Ltd. These examples are not limiting in scope, other resins known to one of ordinary skill in the art can also be used for the above purpose. The resin can also be used as a coating on a secondary structure such as a magnet or a high density material so that the polymer can be recovered from broth magnetically or by methods that rely on adsorbent density such as expanded bed chromatography. Once ansamitocins are adsorbed onto the resin, they can be eluted using one or more organic solvents by means of isocratic or gradient elution. In one embodiment the resin can be added directly to the broth to extract ansamitocins.

Ansamitocins can be recovered from the resin by several means. In one embodiment, the resin can be recovered by filtration. In a second embodiment, the resin can be recovered by centrifugation and the pellet can then be eluted with one or more organic solvents or with one or more organic solvents combined with water. In a third embodiment, aqueous phase and solid debris can be removed from the resin by expanded bed chromatography. The resin can then be compressed in the expanded bed column and eluted with one or more organic solvents or with one or more organic solvents combined with water by isocratic or gradient elution. In a fourth embodiment, the resin can extract ansamitocins while being separated from the fermentation broth by a partially permeable membrane. For example, a dialysis membrane packed with resin can be stirred with fermentation broth, water and low molecular weight components can pass through the membrane, allowing ansamitocins to bind to the resin. The dialysis bag can then be removed from the broth and recovered resin can then be eluted as described above.

Prior to extraction, the microbes in the fermentation broth may be inactivated, if desired, by exposure to mild heating at about 50° to 55° C. for about 30 minutes to 2 hours, or by addition of 1% (v/v) chloroform (Toru Hasegawa et al. 1983, *Int. J. Syst. Bacteriol.* 33:314-320).

Also, prior to or during the extraction, the process can include treatment of the culture medium to facilitate solvent extraction of ansamitocins. The treatment may include but is not limited to heating, adjustment of pH, or enzymatic treatment or chemical treatment, such as the addition of poly ferric sulfate, de-emulsifying agents, fumed silica orcosolvents such as acetone or alcohols such as methanol.

In the case of organic phase extraction, the extraction is carried out at a pH between 2.0-13.0, but preferably at a pH of about 6.0 to 7.0, and more preferably at a pH of about 6.5 to 7.0, and preferably with n-butyl acetate. In order to improve the efficiency of the extraction, broth may be maintained at a temperature between 5° C. and 80° C., preferably between 30° and 45° C. during the extraction process.

The extraction time depends on several factors including the broth composition, the temperature of broth and extraction solvent, the method of mixing broth and solvent and the solvent used for extraction. Extraction time ranges from 1 hour to 120 hours, depending on the extraction method. For example, when a rapid extraction and filtration process is chosen, the extraction time may range between 1-12 hours.

Filter aids may be used during filtration. Such aids include but are not limited to Celpure P1000, Celatom FW-80, Hyflo Super Cel and Celite. Optionally, filter aids can be added directly to the broth during filtration. Optionally, filters may also be pre-coated with a filter aid. Filtration methods that can be used in this process include but are not limited to tangential flow filtration, filter aid coated scraping drum filtration or batch filtration.

In cases where the extraction is performed at pH extremes such as pH 1-pH 5 or pH 8-pH 13 or at highly elevated temperatures such as 60° C.-90° C., the extraction should be completed at a rate which avoids excessive decomposition of the ansamitocins. If necessary, the extraction can also be performed extremely rapidly by continuous centrifugation. In such a case, the pH or temperature of the fermentation broth would be adjusted as broth enters the centrifuge so that prolonged exposure to harsh conditions is avoided. Examples of centrifugal equipment that have been used in fermentation processing and could be used to extract ansamitocins include but are not limited to centrifugal decanters and stacked disc centrifuges. The retained organic solvent extract can then be concentrated under reduced pressure to give a residue that contains the ansamitocins. Alternatively, a water miscible solvent can be mixed with the fermentation broth and centrifuged to remove solids giving a single phase, solid-free solution. The solution can then be processed by, for example, adding a water immiscible solvent to cause the separation of organic and aqueous phases followed by concentration of the organic phase.

Aqueous Washing of Ansamitocins in Solution.

Ansamitocins in a solution of water immiscible organic solvent can be washed with water, aqueous acid, aqueous base, partially or fully salt saturated water or a combination of any of the described aqueous washes. Examples of aqueous acids include but are not limited to aqueous solutions of hydrochloric acid, sulfuric acid, acetic acid, formic acid, and phosphoric acid at a pH between 1-6.9. In the context of this invention, an aqueous acid also includes an acidic aqueous buffered system. Examples of acidic buffered systems include but are not limited to sodium phosphate, potassium phosphate, ammonium acetate, and ammonium formate, each being pH adjusted for use in their respective acidic buffering ranges. Examples of aqueous bases include but are not limited to aqueous solutions of sodium bicarbonate, potassium bicarbonate, sodium carbonate, sodium hydroxide, ammonium hydroxide, and sodium phosphate at a pH between 7.1-13. In the context of this invention, an aqueous base also includes a basic aqueous buffered system. Examples of basic buffered systems include but are not limited to sodium phosphate, potassium phosphate, sodium borate, and ammonium carbonate each being pH adjusted for use in their respective basic buffering ranges.

The acidic or basic washes must be completed without appreciable decomposition of the ansamitocins would vary with the pH. If necessary, extremely rapid extractions can be performed by centrifugal techniques. Examples of partially or fully salt saturated water include but are not limited to aqueous sodium chloride at various levels of saturation, aqueous sodium sulfate at various levels of saturation, and aqueous potassium chloride at various levels of saturation. Aqueous washes can also be performed in which a mixture of a fully or partially saturated aqueous salt solution is combined with an aqueous base or an aqueous acid.

Filtration Prior to Extraction:

Alternatively, prior to extraction, the solids in the ansamitocins containing fermentation broth can be separated by filtration or centrifugation. Ansamitocins in the solid cell mass can be recovered by washing with a solvent such as ethanol, aqueous ethanol, or other organic solvents, such as ethyl acetate, butyl acetate, dichloromethane or acetone, and is well known to one of ordinary skill in the art. The ansamitocins in the filtrate can be recovered by extraction with a known aromatic organic solvent as described elsewhere in the application.

Purification of Ansamitocins:

The crude product can be subjected to purification procedures such as adsorption chromatography over silica gel or alumina, followed by recrystallization if needed. Preferably, the chromatography is conducted on a prepacked column, such as a Biotage silica gel cartridge using the Biotage chromatography system. The desired ansamitocins can be eluted from the column using a solvent gradient starting with a mixture of ethyl acetate and hexane and adding increasing amounts of methanol. The fractions containing the desired ansamitocins can be pooled and concentrated. If desired, the ansamitocins can be further purified by crystallization using a solvent such as ethyl acetate to dissolve the product, and then adding a non polar solvent such as heptane or hexane to crystallize out the pure product. The term crystallization as used herein also encompasses the term precipitation, in that the solid formed from solution can have either an amorphous or a defined structure.

Cell-Binding Agent/Maytansinoid Complexes:

The process of the invention can be used to make cell-binding agent/maytasinoid complexes which are useful as tumor-activated pro-drugs. Ansamitocins prepared by the process of the invention can undergo reductive cleavage to maytansinol which can be used as described in U.S. Pat. Nos. 5,208,020, 5,416,064, 6,333,410 and 6,441,163 to produce N-methyl-L-alanine containing maytansinoid derivatives. These derivatives are then conjugated to cell-binding agents, preferably antibodies, via various linkers such as disulfide-containing linkers.

EXAMPLES

The invention will now be illustrated by reference to non-limiting examples.

Example 1

Production of Ansamitocins

Primary Seed: Seed culture medium VM4-1' (400 ml/flask) comprising of 2% soluble starch, 1% glucose, 1% soybean meal, 0.5% corn steep liquor, (Roquette) 0.5% Soytone, 0.3% sodium chloride, and 0.5% calcium carbonate was poured into each of eleven 2 L capacity Erlenmeyer flasks. After sterilization, each of the flasks was inoculated with the PF4-4 (ATCC PTA-3921) culture. The flasks were incubated at 28° C. on an orbital shaker at 230 rpm for 48 h.

Secondary Seed: The contents of the primary seed flasks were then pooled. A 300 L fermenter was filled with 100 L of the VM4-1' seed medium. After sterilization, the fermenter was inoculated with 4 L of the pooled primary seed culture. The fermenter was maintained at 28° C., with agitation at 80 rpm. The dissolved oxygen level was maintained above 30% saturation by aeration and increased agitation if needed. After incubation for 24 h, the secondary seed culture was ready to be transferred into the production vessels.

Production: Two 300 L production fermenters were each filled with 250 L of production medium FM4-6 (see Table 1). After sterilization, the fermenters were each inoculated with 15 L of the secondary seed culture. The fermenters were maintained at 28° C. with agitation at 107±5 rpm and aeration at 0.4 vvm. After day 2, the dissolved oxygen content was maintained above 30% by increasing the agitation rate to a maximum of 170±5 rpm, and the aeration rate to a maximum of 1 vvm. The ansamitocin titer was measured daily by withdrawing a sample of the fermentation broth and diluting into ethanol, followed by quantitation by HPLC analysis. The fermentation was continued until day 10, at which point, the ansamitocin accretion had leveled off. The ansamitocin titer on day 10 in the two fermenters was 251 mg/L and 244 mg/L respectively. The pH of the fermentation broth was adjusted to 6.5 by addition of phosphoric acid. The fermenters were heated up to 55° C. and maintained at this temperature for 1 h to inactivate the microorganism. The fermenters were then cooled down to ambient temperature for extraction with an organic solvent.

Example 2

Production of Ansamitocins Using a Feed Batch Process

A 1500 L production fermenter was filled with 900 L of production medium FM4-6 (see Table 1). After sterilization, the fermenter was inoculated with 54 L of the secondary seed culture, prepared as described above. The fermenter was maintained at 28° C. with agitation at 107±5 rpm and aeration at 0.4 vvm. From 0 to 48 h, an aqueous solution of 28.5% glucose was fed at a rate of 0.39 mL/L/h. From 48 to 288 h the feed was switched to a stock solution comprising 21.5% glucose, 7.1% Proflo and 7.1% isobutanol, which was fed at the rate of 0.51 mL/L/h. After day 2, the dissolved oxygen content was maintained above 20% by increasing the agitation rate to a maximum of 170±5 rpm, and the aeration rate to a maximum of 1 vvm. The ansamitocin titer was measured daily by withdrawing a sample of the fermentation broth and diluting into ethanol, followed by quantitative analysis by HPLC. The fermentation was continued until day 13, at which point, the ansamitocin accretion had leveled off. The ansamitocin titer on day 13 in the fermenter was 304 mg/L. The pH of the fermentation broth was adjusted to 6.5 by addition of phosphoric acid.

Heat Inactivation. The fermenter was heated up to 55° C. and maintained at this temperature for 1 h to inactivate the microorganism. The fermenters were then cooled to between 30 and 40° C. for extraction with an organic solvent.

Example 3

Extraction and Chromatographic Purification of Ansamitocins

The fermentation broth from Example 2 was mixed with an equal volume of n-butyl acetate. The mixture was maintained between 30 and 40° C. to 45° C., and stirred gently so that mixing of the two phases was just occurring at the solvent interface. The extraction was continued for up to 5 days, or, until HPLC analysis of the organic layer indicated that >80% of the ansamitocins had been extracted. The organic layer was then separated, and evaporated using a falling film evaporator to a final volume of between 20 and 50 L. The concentrated extract was transferred into a flask containing 2.2 kg of silica gel. The crude ansamitocins were coated onto the silica gel by evaporating the solvent to dryness using a rotary evaporator, operating under reduced pressure. The coated silica was then transferred to a sample injection module (SIM), obtained from Biotage, Inc., Charlotesville, Va. The SIM was washed with a mixture of cyclohexane and hexane (2:1 v/v), and then connected to a Biotage 150M system equipped with a silica cartridge. The desired product was eluted from the column using a mixture of ethyl acetate:hexane:methanol (29.4:68.6:2.0, v/v/v). Fractions containing ansamitocins were pooled and the solvent was evaporated under reduced pressure. The product was further dried under high vacuum for 24 h.

Example 4

Recrystallization of Ansamitocins

The dry product from the step above was dissolved in hot ethyl acetate (23 m/g residue). The mixture was maintained between 60-75° C., until complete dissolution of the ansamitocins was achieved. Heptane (80 m/g residue) was added slowly, while maintaining the temperature of the batch between 60-75° C. After all the heptane had been added, the batch was allowed to cool to room temperature. The crystals were recovered by filtration and then dried under high vacuum to give 221 grams of pure ansamitocins.

Example 5

Extraction of Fermentation Broth with Filtration

Fermentation broth (200 mL) prepared as described in Example 2, was vigorously mixed for 5 minutes with 200 mL of n-butyl acetate (200 mL), resulting in an emulsion. Cellatom FW-80 filter aid (20 g) was added, and the mixture was vacuum filtered through a buchner funnel that was pre-coated with Cellatom FW-80 filter aid. The filter cake was washed with 40 mL of n-butyl acetate. The filtrate, now free of solid contaminants, comprising a clear organic and aqueous layer was transferred to a separatory funnel. The aqueous phase was drained. The organic phase containing the ansamitocins was retained.

Example 6

Extraction of Fermentation Broth with Centrifugation Using a Water Immiscible Solvent One part of fermentation broth, prepared as described in Example 2, was vigorously mixed with one part of n-butyl acetate for 2 min. The resulting emulsion was centrifuged for 1 minute and the organic layer containing the ansamitocins, free of solid contaminants, was withdrawn.

Example 7

Extraction of Fermentation Broth with Centrifugation Using a Water Miscible Solvent One part of fermentation broth, prepared as described in Example 2, was vigorously mixed with one part of acetone. The mixture was centrifuged for 1 minute to pellet the solids. Supernatant was withdrawn and mixed with a half part of hexanes. The aqueous layer separated leaving a clear organic phase containing the ansamitocins.

Example 8

Solid Phase Extraction of Ansamitocins using XAD-16 Hydrophobic Beads

One liter of fermentation broth, prepared as described in Example 2, was stirred with 10 grams of XAD-16 beads for six hours. The mixture was then centrifuged and the supernatant was removed. The pellet was transferred to a small column and eluted with deionized water, followed by 90:10 deionized water:acetonitrile. Fractions containing ansamitocins were combined and solvent was evaporated to give 112 mg of concentrated extract. HPLC analysis indicated that the extract contained 50 mg of ansamitocins.

While the invention has been described in detail and with reference to specific embodiments thereof, it will be apparent to one of ordinary skill in the art that various changes and modifications can be made therein without departing from the spirit and scope of the invention.

All publications referred to herein are expressly incorporated by reference.

What is claimed is:

1. A process for preparing purified ansamitocins comprising the steps of:
 1) culturing an ansamitocin-producing microorganism in a liquid culture medium;
 2) solid phase extraction of ansamitocins from the culture medium onto a hydrophobic resin;
 3) isocratic or gradient elution of ansamitocins from the resin using an organic solvent or an organic solvent combined with water;
 4) concentrating the extracted ansamitocins; and
 5) optionally purifying the ansamitocins by any one of a), b), c) and d):
  a) adsorption chromatography over silica gel or alumina,
  b) crystallization,
  c) adsorption chromatography over silica gel or alumina followed by crystallization, and
  d) crystallization followed by adsorption chromatography over silica gel or alumina;

and wherein said ansamitocin has the following structure:

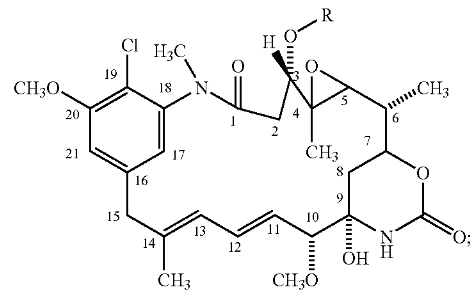

wherein R is H, $COCH_3$, $COCH_2CH_3$, $COCH(CH_3)_2$, $COCH_2CH_2CH_3$, $COCH_2CH(CH_3)_2$ or $COCH_2CH_2CH_2CH_3$.

2. The process of claim 1, wherein the ansamitocin-producing microorganism is *Actinosynnema* spp.

3. The process of claim 1, wherein the ansamitocin-producing microorganism is *Actinosynnema pretiosum.*

4. The process of claim 1, wherein the ansamitocin-producing microorganism is *Actinosynnema pretiosum* ATCC 31565 or a strain derived therefrom.

5. The process of claim 1, wherein the ansamitocin-producing microorganism is *Actinosynnema pretiosum* PF4-4 (ATCC PTA-3921) or a strain derived therefrom.

6. The process of claim 1, wherein said culturing is in production media at a pH in the range of about 6.5 to 8.

7. The process of claim 6, wherein the pH is in the range of about 7 to 7.4.

8. The process of claim 6, wherein the pH is about 7.2.

9. The process of claim 6, wherein the temperature is in the range of about 15° C. to 35° C.

10. The process of claim 6, wherein the temperature is in the range of about 25° C. to 30° C.

11. The process of claim 6, wherein the temperature is about 28° C.

12. The process of claim 6, wherein the temperature is about 28° C. and the pH is 7.2.

13. The process of claim 1, wherein at least one additional nutrient is provided during said culturing.

14. The process of claim 13, wherein the additional nutrient is a carbon source.

15. The process of claim 13, wherein the additional nutrient is a carbon source followed by a carbon source and a protein nutrient.

16. The process of claim 13, wherein there is further provided during the culturing an alcohol or an aldehyde that facilitates the formation of a C-3 ester side chain of the ansamitocin.

17. The process of claim 14, wherein there is further provided during the culturing an alcohol or an aldehyde that facilitates the formation of a C-3 ester side chain of the ansamitocin.

18. The process of claim 15, wherein there is further provided during the culturing an alcohol or an aldehyde that facilitates the formation of a C-3 ester side chain of the ansamitocin.

19. The process of claim 14, wherein the carbon source is glucose.

20. The process of claim 15, wherein the carbon source is glucose.

21. The process of claim 17, wherein the carbon source is glucose.

22. The process of claim 18, wherein the carbon source is glucose.

23. The process of claim 15, wherein the protein nutrient is cotton seed flour or soybean flour.

24. The process of claim 18, wherein the protein nutrient is cotton seed flour or soybean flour.

25. The process of claim 16, wherein the aldehyde or alcohol is selected from the group consisting of isobutanol, isobutyraldehyde, n-butanol, n-butyraldehyde, n-propanol, n-propionaldehyde, isopropanol, isopropionaldehyde, pentanol, valeraldehyde, isopentanol, and isovaleraldehyde.

26. The process of claim 17, wherein the aldehyde or alcohol is selected from the group consisting of isobutanol, isobutyraldehyde, n-butanol, n-butyraldehyde, n-propanol, n-propionaldehyde, isopropanol, isopropionaldehyde, pentanol, valeraldehyde, isopentanol, and isovaleraldehyde.

27. The process of claim 18, wherein the aldehyde or alcohol is selected from the group consisting of isobutanol, isobutyraldehyde, n-butanol, n-butyraldehyde, n-propanol, npropionaldehyde, isopropanol, isopropionaldehyde, pentanol, valeraldehyde, isopentanol, and isovaleraldehyde.

28. The process of claim 13, wherein the culturing is at a pH of about 6.5 to 8.

29. The process of claim 13, wherein the culturing is at a pH of about 7 to 7.4.

30. The process of claim 13, wherein the culturing is at a pH of about 7.2.

31. The process of claim 13, wherein the culturing is at a temperature of about 15° C. to 35° C.

32. The process of claim 13, wherein the culturing is at a temperature of about 25° C. to 30° C.

33. The process of claim 13, wherein the culturing is at a temperature of about 28° C.

34. The process of claim 13, wherein the culturing is at a temperature of about 28° C. and a pH of 7.2.

35. The process of claim 1, further comprising the steps of:
   (i) chemical or heat inactivation of the microorganisms in the culture medium or;
   (ii) treatment of the culture medium to facilitate solvent extraction of ansamitocins, prior to step 2 or;
   (iii) a washing step in which a crude solution of ansamitocins in the organic solvent is washed with water, an aqueous salt solution, an aqueous acid or an aqueous base in any sequential combination, before or after the precipitation which can be performed during the purification; or a combination of any of (i), (ii), and (iii).

* * * * *